US007267847B2

(12) United States Patent
Karamuk

(10) Patent No.: US 7,267,847 B2
(45) Date of Patent: Sep. 11, 2007

(54) HYDROPHOBIC COATING OF INDIVIDUAL COMPONENTS OF HEARING AID DEVICES

(75) Inventor: Erdal Karamuk, Zurich (CH)

(73) Assignee: Phonak AG, Stafa (CH)

( * ) Notice: Subject to any disclaimer, the term of this patent is extended or adjusted under 35 U.S.C. 154(b) by 561 days.

(21) Appl. No.: 10/749,291

(22) Filed: Dec. 30, 2003

(65) Prior Publication Data

US 2005/0141738 A1 Jun. 30, 2005

(51) Int. Cl.
*H05H 1/24* (2006.01)
*A61L 33/00* (2006.01)

(52) U.S. Cl. ........................................ 427/569; 427/2.1

(58) Field of Classification Search ................ 418/569, 418/2.1
See application file for complete search history.

(56) References Cited

U.S. PATENT DOCUMENTS 5,674,624 A * 10/1997 Miyazaki et al. ........... 428/422
6,649,222 B1 * 11/2003 D'Agostino et al. ........ 427/490
6,751,327 B1 * 6/2004 Urso et al. .................. 381/323
2001/0049051 A1 * 12/2001 Jones et al. ................... 429/86
2004/0179709 A1 * 9/2004 Niederdraenk et al. ..... 381/322

FOREIGN PATENT DOCUMENTS

DE 100 51 182 A 5/2002
DE 101 06 213 A 8/2002
EP 0 629 101 A 12/1994
WO 99/45744 A 9/1999
WO 03/094574 A 11/2003

OTHER PUBLICATIONS

Davies, Gareth. "Vapour Permeable Paint" from "The Building Conservatory Directory, 1996" Accessed from http://www.buildingconservation.com/articles/vapour/vapour.htm on May 16, 2007.*

* cited by examiner

*Primary Examiner*—Timothy Meeks
*Assistant Examiner*—Kelly M Stouffer
(74) *Attorney, Agent, or Firm*—Pearne & Gordon LLP

(57) ABSTRACT

For the liquid impervious sealing of smallest crevices, chinks, capillaries and/or openings within a housing wall, in particular of electronic or electrical devices, it is proposed to provide the housing wall at least in the area of the crevices, chinks, openings or capillaries with a hydrophobic coating. The advantage of applying a hydrophobic coating is that certain gas permeability can be maintained, so that a gas exchange between the interior of the housing and the environment is possible.

17 Claims, 3 Drawing Sheets

HYDROPHOBIC COATING OF INDIVIDUAL COMPONENTS OF HEARING AID DEVICES

BACKGROUND OF THE INVENTION

The present invention refers to a process for the sealing of smallest crevices, chinks and/or openings in walls of housings against penetration of fluids, the use of the process, housings of electrical or electronic devices having crevices, capillaries, chinks, openings and the same which have to be sealed against penetration of fluids, but not against penetration of gases as well as a battery compartment of a hearing aid device.

In particular with medical devices which are worn on the human body, there exists the danger that under the influence of humidity, perspiration, etc. certain parts and components of the device may corrode and not operate properly anymore. Especially penetration of fluids and perspiration into hearing aid devices may cause corrosion e.g. of the battery and in certain cases may cause disturbances of the electronic as well as of the electro-acoustical transducer. Correspondingly, various processes are described to make hearing aid devices more resistant against penetration of fluids.

In the DE 19502994A1 a watertight hearing aid device is described in which the characteristic of water tightness is achieved by complicated constructive measures such as gaskets and membranes. The DE 3834316C1 describes a completely watertight hearing aid device but does not show, compared to the patent application mentioned before, in detail how the water tightness is achieved but lays more stress on describing in detail the design of watertight operating elements. Again, in the JP 11069498, the U.S. Pat. No. 5,249,234A and the U.S. Pat. No. 6,510,230B2 various approaches are described to protect HdO-devices by using a protection envelope against the penetration of humidity. This protection envelope contains, according to the design, also materials to absorb perspiration or humidity.

In the US 2002/0181725A1 a condenser-microphone with a hydrophobic membrane is described to prevent the sticking together with the backplate and also various methods how the hydrophobic characteristic can be achieved.

The US 2002/100605A1 describes a hydrophobic coating for housings of electrical devices, in particular in relation to over-voltage conductors. Again, in further documents hydrophobic coatings of substrates are described, such as polymers, wood, concrete, etc., for which the above mentioned problem is no topic.

In particular medical devices which are worn on the human body, such as pulse frequency measuring devices, invasive detecting sensors for blood characteristics, such as oximetry-sensors, heart frequency measuring devices, hearing aid devices and the same are usually complicated devices which consist out of a plurality of individual mechanical or electronic components which are produced by using various processes and are finally assembled. Due to the mechanical tolerances of the injection moulding, plastic parts which in most cases are used for housings, battery compartment covers, switches and the same, microscopic capillary crevices can always accrue between the individual components also at the assembled status of the devices.

As most of these medical devices, such as e.g. hearing aid devices, are operated with zinc-air-batteries, it is not possible to close the device hermetically, as the battery needs a constant supply of oxygen to maintain the operation voltage. Of course, this requirement is also possible for other electronic or electrical components which need certain aeration. The consequence is that a complete impermeability, as it is described partly in the state of the art, is not suitable. Also complicated mechanical constructions with the use of gaskets and porous membranes, as they are known out of the state of the art, are not appropriate and make medical devices usually bigger and more expensive.

It is very difficult to envisage the influence of capillary crevices by designing a hearing aid device or generally of a smallest medical device. But as mechanical constructions for preventing penetration of liquids at existing device designs are not any more possible without any difficulties, it is a subject of the present invention to make medical devices, as in particular smallest devices and hearing aid devices, permeable without the need of changing, the design. It is also essential that at the complete sealing against penetration of humidity still a certain permeability of gas is present within the capillary crevices.

With the development of hearing aid devices and the same, the trend is going more and more into the direction of modular components which can be combined for constructions of different devices. To reduce working hours and costs and the improvement of reproducibility, also for so called in-the-ear hearing aid devices, an improved modularity is aspired. The inherent problems with modular systems are the mentioned capillary crevices which may accrue at the assembling of the individual modules to a device. Through these capillaries the penetration of fluids into the hearing aid device is accelerated.

Finally, the possibility fails to produce the hearing aid device out of a water repellent hydrophobic material which could reduce the wettability and therefore the penetration of fluids through capillary crevices fails, as it would not change anything about the fact that such materials like Teflon can neither be processed by ordinary processes, nor the mechanical and aesthetic criteria may be achieved.

SUMMARY OF THE INVENTION

To solve the above mentioned problem according to the present invention, it is proposed to protect individual components or areas of a casing wall of an electrical or electronic device, such as in particular a medical device, by specific hydrophobic coating in the area of the mentioned capillary crevices, chinks and the same against the penetration of a fluid, as the hydrophobic coating (hydrophobisation) of the individual components or housing areas is reducing the surface energy of the material. As a consequence, the liquid droplets, such as water, perspiration and the like, cannot spread on the surface of the component or housing areas but will contract with a higher contact angle, as it is shown in FIGS. 1*a*, 1*b* and 2. Therefore, it is more difficult for a liquid droplet to penetrate the interior of the medical device through the capillary crevices, such as e.g. a hearing aid device. However, the capillary crevices or chinks remain gas permeable and there are no seals arranged, so that the above mentioned gas exchange with the environment is guaranteed, such as e.g. the oxygen supply of zinc-air-batteries.

BRIEF DESCRIPTION OF THE DRAWING

The invention will now be explained in more detail based on design examples and with reference to the attached drawings in which:

FIG. 1*a* shows the contact angle of water 1 on an untreated or uncoated surface 3, as e.g. of a polymer, which is used for components of hearing aid devices. Exemplary used polymers are e.g. polyamide, ABS. etc. The contact angle, according to FIG. 1*a* is substantially below 80°.

DETAILED DESCRIPTION OF THE EXAMPLE EMBODIMENTS

Figure 1A:
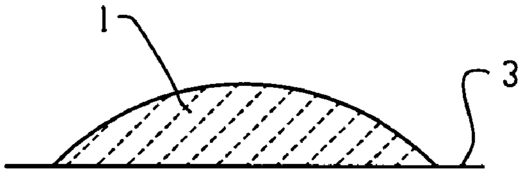
FIGS. 1*a* & 1*b* show the influence of a hydrophobic coating on the wettability of the coated surface or the contact angle of water on the surface.
Figure 1B:
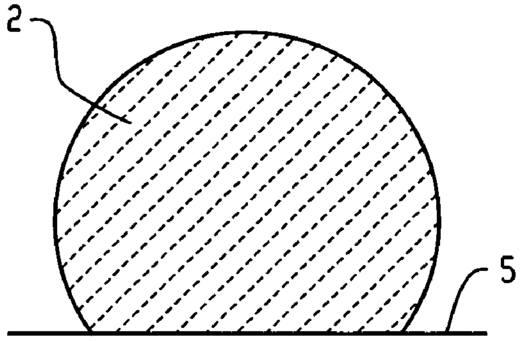

By applying a hydrophobic coating on the surface 5 as shown in FIG. 1*b*. the contact angle of water 2 can be increased substantially, as e.g. above 100°, which is equivalent to the wettability of Teflon.

Figure 2:
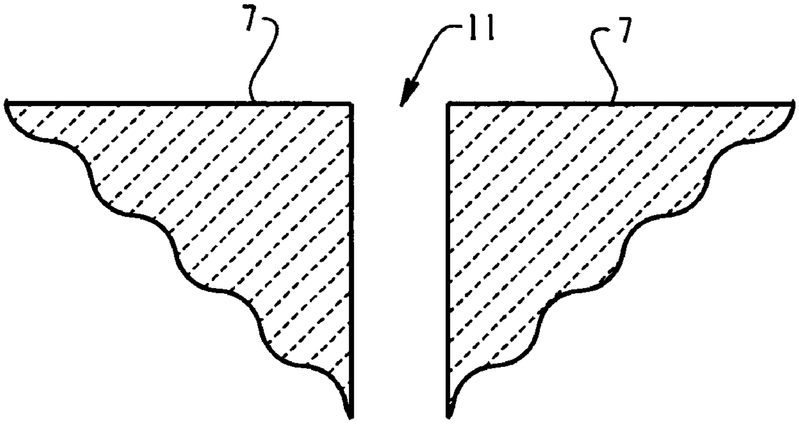
FIG. 2 is a cross-section view of a capillary opening or a chink within a wall of a casing like e.g. of a hearing aid device

In FIG. 2 schematically in cross-section view, a capillary crevice 11 is shown, as it can be shaped within a wall 7 of the casing of a hearing aid device. The comparison of the two FIGS. 1*a* and 1*b* shows clearly that a water droplet, according to FIG. 1*a*, can penetrate easily through the capillary 11, while the water droplet, according to FIG. 1*b*, remains on the surface on the wall of the casing, as the penetration through the capillary 11 is impossible. But as there are no sealing means, such as e.g. a rubber seal and the like within the capillary, the gas permeability nevertheless can be maintained.

Figure 3:
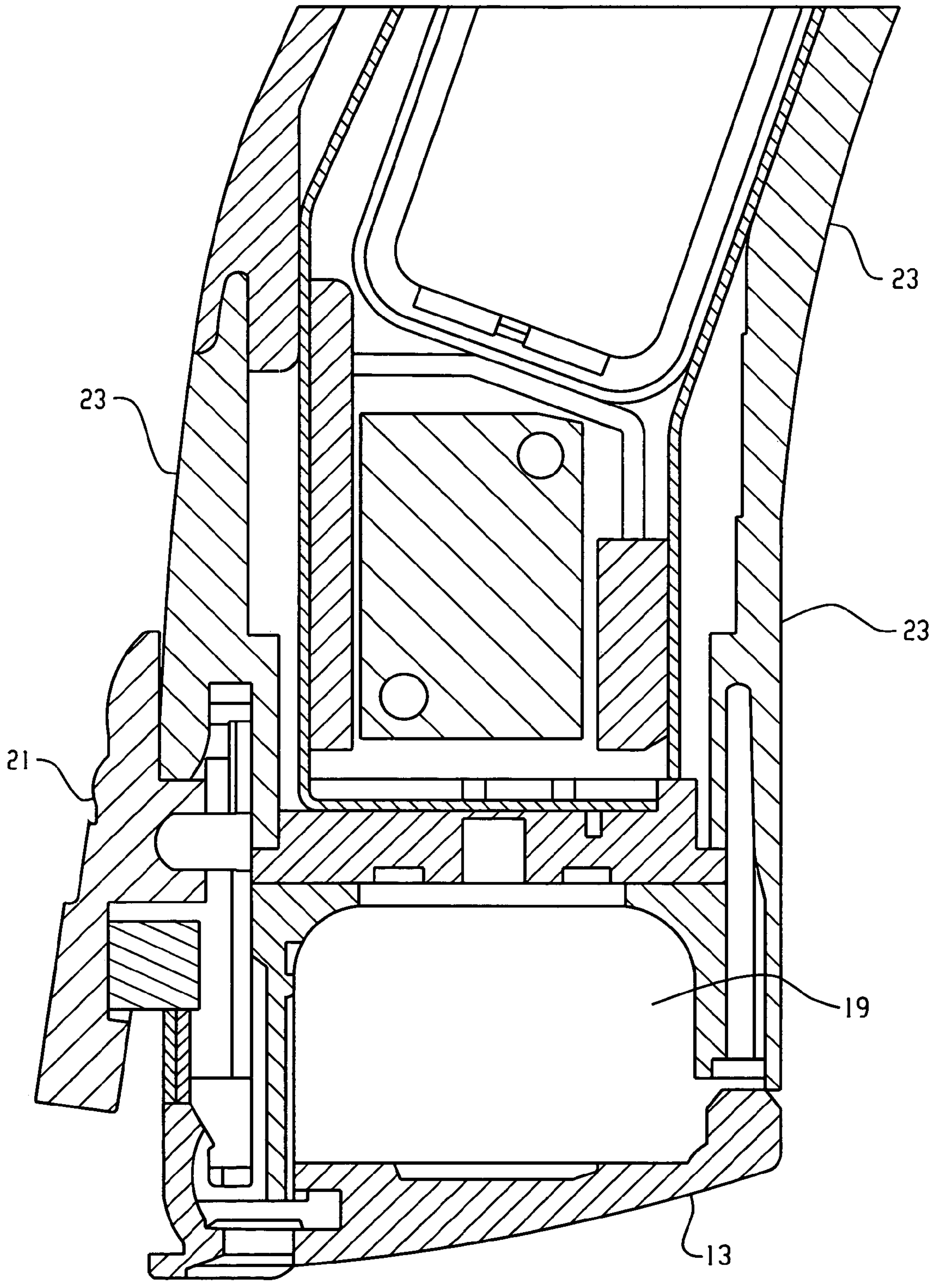
FIGS. 3 & 4 show each in a cross-section view an example of a battery case within a hearing aid device.
Figure 4:
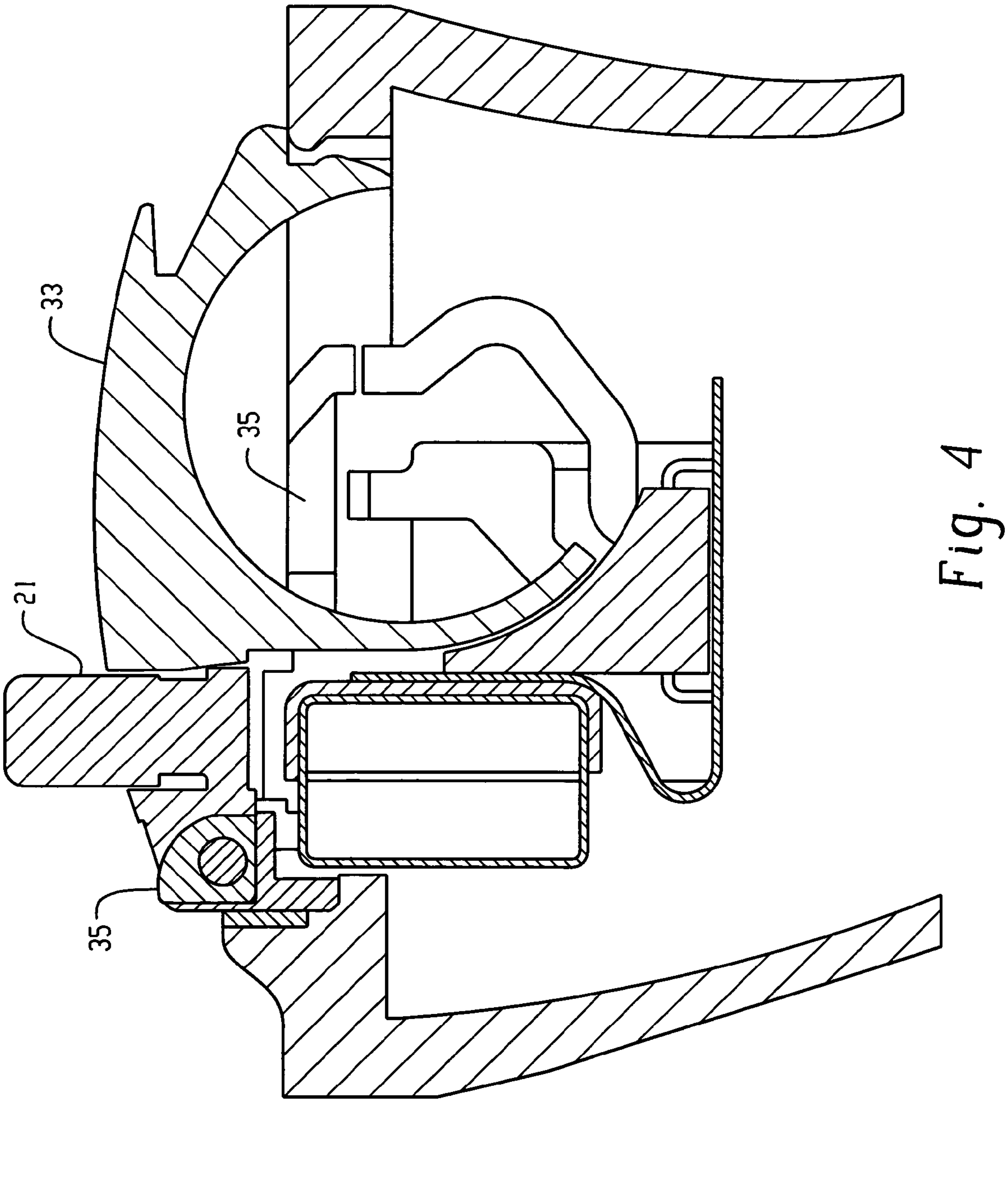

By means of the two FIGS. 3 and 4, concrete examples are to be shown which describe components, such as battery compartments of a hearing aid device which has to be sealed, according to the subject of the present invention.

FIG. 3 shows in cross-section view the area of a battery compartment of a known hearing aid device which is sealed against penetration of a liquid. It is essential that all parts of the casing which are arranged in the area of the battery compartment 19 are provided with a hydrophobic coating. These parts are the battery cover 13, the mentioned battery compartment 19, the casing 23, as well as the function switch 21.

The individual components are coated after their manufacturing or delivering and prior to the assembling into a hearing aid device. For a casing, such as e.g. shown in FIG. 3, the consequence is e.g. that after the injection moulding it first has to be cleaned, and then pre-treated, if necessary, so that afterwards it can be coated hydrophobically by a process as will be described later on.

Which components of a specific hearing aid device design have to be coated to achieve a most effective protection against the penetration of a liquid, has to be evaluated for each hearing aid device individually. Basically, various components have to be coated to achieve a hydrophobisation on all sides of a capillary system, as described e.g. with reference to FIG. 3.

FIG. 4 shows a further design of a battery compartment of a hearing aid device and again those parts or components of the casing of the device are to be designated which have to be provided with a hydrophobic coating. These parts are e.g. a function switch 21 (e.g. a pushbutton), the battery cover 33, as well as a frame 35.

Unlike the various above mentioned solutions to make devices impermeable against penetration of liquids in the present invention, a protection against liquid penetration is achieved by a selective surface treatment of individual components of an electrical or electronic device, such as e.g. of individual components of a hearing aid device. The process to be used to apply a hydrophobic coating on the components is of secondary importance for the present invention, as a plurality of suitable processes is known out of the state of the art. Following, some processes should be mentioned as examples for the better understanding of the present invention.

Basically, chemical and physical coating processes are suitable. Known are e.g. coatings by using so called Sol-Gel processes. These processes are known from the chemical nanotechnology. The surface is coated with hydrophobic nano-particles which are included within a polymer network. The coatings are composite materials (nano-composites) with organic and inorganic components which are produced by using Sol-Gel processes. The coating is applied by using simple dipping- or spraying processes followed by a hardening process. In principal, all those coatings can be applied to all kind of materials which can withstand the necessary temperatures for the hardening process. For the most materials which are used for the production of hearing aid devices, coatings by using Sol-Gel processes are possible. By selecting the individual chemical components, the properties of the surface can be adjusted and the hydrophobic or also the anti-microbial effect can be achieved, as e.g. described within the WO 03/094574.

The advantage of this coating lies in the simple handling and the low operating expenditure that is needed.

Nano-particles with hydrophobic and oleophobic properties and their application are also described e.g. within the DE 10051182A1, DE 19544763A1 or DE 19948336A1. Further processes for hydrophobic coatings on polymer surfaces can be found within the US 2002/0192385A1 or the DE 10106213A1.

Of course, also further chemical processes are known for hydrophobic coatings such as e.g. by using coatings made out of hydrated silanes (hydro-silicones), fluorine containing poly-condensate coatings, etc.

Besides chemical processes also physical processes, as e.g. coatings by using plasma processes, are suitable.

The coating is applied by using low temperature plasma evaporation processes. Within the same production step, the surface is cleaned and activated (e.g. by using an oxygen plasma) and afterwards coated. With the coating, either a compact polymer coating made out of a fluorine containing polymer is applied to the component, or a hydrophobic molecule is attached directly to the plastics of the component.

The advantages of the present invention are the following:

Due to the hydrophobic coatings, e.g. in the area of a battery compartment, the vulnerability to corrosion within an electronic smallest device, such as e.g. a medical device, as in particular a hearing aid device, can be reduced by preventing the liquid to enter or can even be excluded completely.

The inventive process can be applied to products which already have been introduced on the market. The improvement of resistance against liquid penetration is even possible without the change of the design. A device can be equipped while in operation with components which are coated with a hydrophobic coating.

The intervals between maintenance operations due to contamination or corrosion can be expanded, which means the device does have longer life time durability.

At modular electronic devices, such as medical devices or hearing aid devices with many capillary crevices, the reduction or the prevention of water entrance is possible. As a consequence, complex mechanical sealing is not necessary anymore and the devices can be built in a smaller and less costly manner.

The invention claimed is:

1. Process for the liquid impervious sealing of one or more of small crevices, chinks, capillaries and openings in a wall of a hearing device housing which occur due to an assembly of at least two structural components of the hearing device, wherein at least certain gas permeability has to be obtained, said method comprising the step of providing a hydrophobic coating on the housing wall at least in the area of the one or more of crevices, chinks, openings and capillaries to prevent moisture from an exterior of said housing wall from entering the one or more of crevices, chinks, openings and capillaries.

2. Process according to claim 1 for the liquid impervious sealing of housing chambers, compartments, sections which are closed against the exterior and at which a certain gas exchange with the environment has to be guaranteed, wherein, in the area of the chamber, the compartment or the section crevices, and the one or more chinks, capillaries, and openings which exist within the housing wall, are provided with a hydrophobic coating.

3. Process according to one of the claims 1 or 2, wherein the housing or casing wall or its surface in the area of the one or more crevices, chinks, capillaries and openings, shall be coated with hydrophobic nano-particles.

4. Process according to one of the claims 1 or 2, wherein the hydrophobic coating, by using hydrophobic nano-particles, is produced by a so called Sol-Gel process.

5. Process according to one of the claims 1 or 2, wherein the hydrophobic coating is achieved by coating of the housing wall with the aid of hydrated silanes or hydro-silicones or fluorine containing polycondensates.

6. Process according to one of the claims 1 or 2, wherein the coating is executed by using a low temperature plasma evaporation process, the coating of a compact polymer layer is achieved by depositing a fluorine containing polymer on the housing wall.

7. Process according to one of the claims 1 to 2 for the liquid impervious sealing of the one or more crevices, chinks and capillary openings in housing walls of hearing aid devices.

8. Process according to one of the claims 1 to 2 for the liquid impervious sealing of a battery compartment in a hearing aid device.

9. Process according to claim 3, wherein the hydrophobic coating, by using hydrophobic nano-particles, is produced by a Sol-Gel process.

10. Process according to claim 5 for the liquid impervious sealing of the one or more of crevices, chinks and capillary openings in housing walls of a hearing aid device.

11. Process according to claim 5 for the liquid impervious sealing of a battery compartment in a hearing aid device.

12. Process according to claim 6 for the liquid impervious sealing of the one or more crevices, chinks and capillary openings in housing walls of a hearing aid device.

13. Process according to claim 6 for the liquid impervious sealing of a battery compartment in a hearing aid device.

14. Process according to claim 1, wherein said coating is applied to an exterior surface of said housing wall.

15. Process for the liquid impervious sealing of small gaps between components of a hearing aid device, said method comprising the steps of:

assembling at least two components of said hearing aid device together to form a surface having said small gaps, wherein said surface is gas permeable;

coating at least a portion of said surface in the area of said gaps with a hydrophobic coating to prevent penetration of a liquid into said gaps from an exterior of said surface , wherein said portion of said surface remains gas permeable with said hydrophobic coating thereon.

16. Process according to claim 15, wherein the hydrophobic coating is achieved by coating of the portion with the aid of hydrated silanes or hydro-silicones or fluorine containing polycondensates.

17. Process according to claim 15 wherein said surface is provided at an exterior of said hearing aid device, and wherein said coating is applied to the exterior of said surface.

* * * * *

UNITED STATES PATENT AND TRADEMARK OFFICE

CERTIFICATE OF CORRECTION

PATENT NO. : 7,267,847 B2
APPLICATION NO. : 10/749291
DATED : September 11, 2007
INVENTOR(S) : Erdal Karamuk et al.

It is certified that error appears in the above-identified patent and that said Letters Patent is hereby corrected as shown below:

On the title page:

Item (75), Inventor, please insert the following 2 inventors:

--Stefan Launer, Zurich (CH)--

--Michael Mathey, Jona (CH)--

Signed and Sealed this

Twenty Second Day of April, 2008

JON W. DUDAS
*Director of the United States Patent and Trademark Office*